United States Patent [19]

Takeda et al.

[11] Patent Number: 5,026,875

[45] Date of Patent: Jun. 25, 1991

[54] STABILITY-IMPROVED TRIOXANE COMPOSITION

[75] Inventors: Mutsuhiko Takeda, Tokyo; Minoru Kakuda, Matsudo; Masafumi Shimpo, Kashiwa; Kiyoshi Yoshida, Tokyo, all of Japan

[73] Assignee: Mitsubishi Gas Chemical Company, Inc., Tokyo, Japan

[21] Appl. No.: 343,675

[22] Filed: Apr. 27, 1989

[30] Foreign Application Priority Data

May 23, 1988 [JP] Japan ................................. 63-123941

[51] Int. Cl.$^5$ ............................................ C07D 326/06
[52] U.S. Cl. .................................... 549/201; 549/200; 549/368; 549/75; 548/505
[58] Field of Search ............... 549/201, 200, 202, 203, 549/204, 368, 75; 564/26, 253; 514/452; 548/505

[56] References Cited

U.S. PATENT DOCUMENTS

| | | | |
|---|---|---|---|
| 2,226,427 | 12/1940 | George et al. | 564/253 |
| 2,388,255 | 11/1945 | Daskais et al. | 564/253 |
| 2,939,882 | 6/1960 | Mecorney | 564/253 |
| 4,045,551 | 8/1977 | Veno et al. | 514/452 |
| 4,125,540 | 11/1978 | Sugio et al. | 549/201 |

FOREIGN PATENT DOCUMENTS 43-544  3/1968  Japan .................................. 549/201

Primary Examiner—Richard L. Raymond
Assistant Examiner—Mark W. Russell
Attorney, Agent, or Firm—Sherman and Shalloway

[57] ABSTRACT

Disclosed is a composition comprising 1,3,5-trioxane, and more particularly a stability-improved trioxane composition.

18 Claims, No Drawings

STABILITY-IMPROVED TRIOXANE COMPOSITION

BACKGROUND OF THE INVENTION

1. Field of the Invention

The present invention relates to a composition comprising 1,3,5-trioxane, and more particularly to a stability-improved trioxane composition.

2. Description of the Related Art

Generally, 1,3,5-trioxane (hereinafter called "trioxane") is used for a resin intermediate and for an effective component of an insect-proofing agent.

Trioxane is a substance which is normally stable at room temperature. However, when heated and kept in a melted state for a long time in air, this substance is decomposed and oxidized in part to produce formaldehyde and formic acid and, at the same time, is polymerized in part to produce unsoluble polyoxymethylene.

Further, even in room temperature, when a solid substance having activity, such as an active silica, is in direct contact with trioxane in a solid or liquid state, or when the substance is disposed adjacent to trioxane in a solid or liquid state to contact trioxane vapor, trioxane is decomposed at the active site of the solid substance to produce formaldehyde and formic acid.

Meanwhile, thanks to advanced technology of modern industry, high-purity trioxane can be obtained, but occasionally happens to contain a small amount of formaldehyde as impurities.

Formaldehyde is a gas having an irritating odor; when the concentration of formaldehyde in trioxane is over 16 ppm by weight, the odor of formaldehyde can be felt by men. In the case trioxane is used for an insect-proofing agent, for example, comfortable use or handling cannot be achieved because of the odor. Consequently, when trioxane is used as an insect-proofing agent, the preferred concentration of formaldehyde in trioxane is less than 16 ppm by weight, especially not more than 8 ppm by weight.

Further, since formic acid promotes the decomposition of trioxane, it is necessary to prevent the production of formic acid.

However, heretofore, there has been proposed no effective idea to prevent trioxane from being decomposed and polymerized due to heat and also to prevent trioxane from being decomposed due to an active solid substance and additionally to reduce the concentration of formaldehyde to be contained at the stage of production. Thus there is known no way of satisfying those requirements at the same time and of increasing the stability.

SUMMARY OF THE INVENTION

With the foregoing problems in view, the present inventors have made various investigations on additives to trioxane. As a result, the inventors have discovered that it is possible to obtain an increased stability by adding a keto-oxime compound to trioxane. Based on this discovery, the inventors have developed a new composition free from the above conventional problems.

It is accordingly an object of the present invention to provide a trioxane composition in which trioxane can be prevented from being decomposed or polymerized due to heat and also can be prevented from being decomposed by an active solid substance, thereby to provide the trioxane composition of increased stability.

Another object of the invention is to provide a trioxane composition in which the concentration of each of formaldehyde and formic acid in trioxane can be maintained at a remarkably low level.

Still another object of the invention is to provide a trioxane composition which is useful for insect-proofing agents, especially an insect-proofing agent for clothing.

According to the present invention, there is provided a trioxane composition which comprises 1,3,5-trioxane and a keto-oxime compound and in which the stability of the trioxane is increased.

DETAILED DESCRIPTION OF THE PREFERRED EMBODIMENTS

The keto-oxime compound (hereinafter called "keto-oxime") used in the present invention is a compound having a partial structure [$>C=N-OH$] and may be represented by the following general formula (I) through (VI), for example.

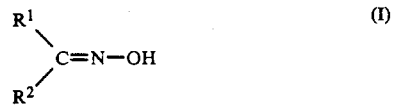

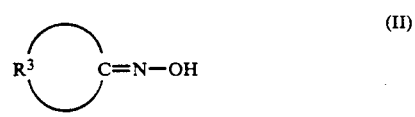

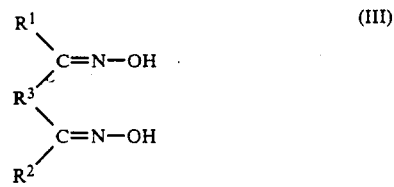

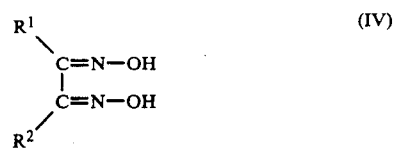

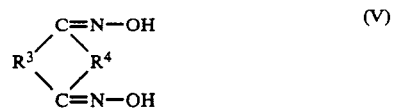

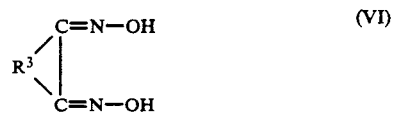

wherein each of $R^1$ and $R^2$ represents, for example, an alkyl group, a substituted alkyl group, a phenyl group, a substituted phenyl group, a monovalent heterocyclic group or an acyl group, and each of $R^3$ and $R^4$ represents, for example, an alkylene group, a substituted alkylene group or a diphenylene group.

Alkyl group is exemplified by a straight chain alkyl group or a branched chain alkyl group each having not more than 5 carbon atomes. Its substituent is a neutral substituent, such as an alkoxy group or a hydroxyl group, or a basic substituent such as an amine group. When $R^1$ or $R^2$ is a phenyl group, this phenyl group may have a substituent such as an alkyl group or an alkoxy group. Further, $R^1$ and/or $R^2$ may be a monovalent heterocyclic group, such as a furyl group, a thienyl group or an indolyl group. Acyl group may be a lower acyl group such as an acetyl group. The number of carbon atom of alkylene group or a substituted alkylene group as $R^3$ and/or $R^4$ varies depending on the formula (II), (III), (V) or (VI); but generally the preferred number of carbon atoms is within the range of 3 to 9.

Typical examples of ketoxime compounds used in the present invention are as follows.

Examples of the ketoxime represented by the formula (I) and containing an alkyl group alone include acetoxime, ethylmethylketoxime, diethylketoxime, methyl n-propylketoxime, methylisopropylketoxime, methylisobutylketoxime, pinacolinoxime, di-n-propylketoxime, diisopropylketoxime and methylisoamylketoxime. Examples of the ketoxime represented by the same formula but containing a substituted alkyl group are acetoinoxime and methyloximisopropylketoxime; those containing a phenyl group are acetophenone-oxime, propiophenonoxime, butyrophenonoxime, valerophenonoxime, benzophenonoxime and benzoinoxime; that containing a substituted phenyl group is 4-chloroacetophenonoxime; that containing a acyl group is diacetylmonoxime; those containing a monovalent heterocyclic group are 2-acetofuronoxime and 2-acetothienone-oxime.

Examples of the ketoxime represented by the formula (II) and containing an alkylene group includes cyclobutanonoxime, cyclopentanonoxime and cyclohexanonoxime; that containing a substituted alkylene group is camphor-oxime; that containing a diphenylene group is 9-fluorenonoxime.

The ketoxime having two oxime units in the molecule and represented by the formula (III) is acetylacetonedioxime; those represented by the formula (IV) are dimethylglyoxime, diphenylglyoxime and furyldioxime.

The ketoxime having two oxime units in the molecule and having a cyclic structure and represented by the formula (V) is dimedone-dioxime; that represented by the formula (VI) is nioxime.

According to the present invention, the following results can be achieved:

(a) Trioxane melted by heat in air can be prevented from being decomposed or polymerized.

(b) Trioxane at the active surface of a solid can be prevented from being decomposed.

(c) Formaldehyde contained in trioxane can be captured to thereby reduce its concentration.

The action of ketoxime is to prevent decomposition of trioxane and, at the same time, to combine with formaldehyde which exists in a little amount in trioxane. Regarding the above-mentioned result (b), the oxime vapor is adsorbed to the active site of the solid so that the chemical activity of the solid can be missed out. Therefore, in order to expect the above result (b) with the solid disposed out of direct contact with and adjacent to trioxane so as to contact trioxane vapor only, it is preferred that the oxime having a high vapor pressure be incorporated. Such an additive is a ketoxime compound containing not more than ten carbons; especially acetoxime, ethylmethylketoxime, methylisoamylketoxime and cyclohexanonoxime are easily available and are hence preferred.

In the present invention, the concentration of formaldehyde in trioxane as a raw material is not limited to a specific value, but practically the preferred concentration is 100 ppm by weight or less, especially 50 ppm by weight or less. When the concentration of formaldehyde in the raw material trioxane is 16 ppm by weight or less, or 8 ppm by weight or less, an additional reduction of the concentration of formaldehyde can be achieved by the present invention.

The amount of ketoxime to be incorporated in the present invention cannot be specified as it can be varied depending on the quality of the raw material trioxane, the required characteristics of the composition. Generally, the preferred content of ketoxime in the trioxane composition is 0.05 to 10% by weight, especially 0.1 to 2% by weight. If the amount of the incorporated ketoxime is too small, adequate results cannot be expected. Further, for the amount of ketoxime to be incorporated, the above-mentioned range is enough, and no more incorporation is required. Also when two or more kinds of ketoxime compounds are used, it is enough that the sum amount of these compounds is in the above-mentioned range.

In the trioxane-containing composition of the present invention, a lubricant, a perfume, a stabilizer, etc may be incorporated according to need.

In the present invention, the way of incorporating of ketoxime is not limited to a specific method. For example, a predetermined amount of ketoxime may be put in a molten trioxane and mixed therewith preferably in an inert atmosphere such as nitrogen, whereupon the resulting mixture may be cooled to form a solid composition.

According to the trioxane-containing composition of the present invention, it is possible to keep trioxane stable without producing any decomposed product or polymerized product such as formaldehyde, formic acid or polyoxymethylene.

The following examples illustrate the present invention more specifically.

EXAMPLES 1 THROUGH 5

To 60 grams of trioxane in a molten state containing 6.3 ppm by weight of formaldehyde and 1.3 ppm by weight of formic acid as impurities, a predetermined amount of various kinds of ketoxime was added. In the presence of air, the mixture was put in a 100 ml. Kjeldahl flask, and then the flask was closed with a lid to keep the mixture in a molten state at a temperature of 65° to 75° C. Three days later, part of the resultant liquid was sampled and was dissolved in water. The concentration of formaldehyde in this aqueous solution was measured by 3-methyl-2-benzothiazole hydrazone test (hereinafter refer to MBTH) (ANALYTICAL CHEMISTRY Vo. 13, No. 1, p93-96) and was shown in Table 1 as the content based on the trioxane (wt ppm). Also, the concentration of formic acid in the aqueous solution of trioxane was measured by titration and was shown in Table 1 as the content based on the trioxane (wt ppm).

Further, after the above sampling, about 50 grams of the rest of the liquid were left deposited until the liquid was cooled to become solid, whereupon the solid was melted again by heat. As a result, there was found no precipitate due to the polymerized substance.

COMPARATIVE EXAMPLE 1

The same experiment as in Examples 1-5, except that ketoxime was not added to the molten trioxane, was conducted to keep the trioxane in a molten state. Three days later, the concentration of formaldehyde and the concentration of formic acid in trioxane were measured. The results are shown in Table 1.

Further, after the sampling, about 50 grams of the rest of the liquid were left deposited until the liquid was cooled to become solid, whereupon the solid was again melted by heat. As a result, there was found a white precipitate polyoxymethylene due to polymerization in the liquid trioxane.

TABLE 1

| Example No. | ketoxime (kind) | trioxane (wt %) | ketoxime (wt %) | form- aldehyde (wt ppm) | formic acid (wt ppm) |
| --- | --- | --- | --- | --- | --- |
| 1 | ethylmethyl- ketoxime | 99.0 | 1.0 | 9.7 | 199.2 |
| 2 | ethylisoamyl- ketoxime | 99.9 | 0.5 | 15.0 | 250.0 |
| 3 | cyclohexanon- oxime | 99.0 | 1.0 | 7.4 | 144.0 |
| 4 | fluolenoneoxime | 98.5 | 1.5 | 6.0 | 120.0 |
| 5 | nioxime | 99.5 | 2.0 | 4.0 | 80.0 |
| Comparative Example 1 | — | 100 | 0 | 314.4 | 995.9 |

EXAMPLES 6 AND 7

98.5 to 99.9 parts by weight of trioxane containing neither formaldehyde nor formic-acid, and 1.5 to 0.1 parts by weight of various kinds of ketoxime compounds were mixed, and the mixture was melted in a hot water bath to form a uniform liquid, whereupon the liquid was cooled to 20° C. to obtain a solid composition. Then the solid composition was compressed and shaped by a tablet forming device to prepare tablets each weighing 2.0 grams.

20 grams of granular Silica Gel Blue (product by Koso Chemical Co., Ltd.) were put on the bottom of an 11-liter brown glass bottle. Above the silica gel, a net bag of polyethylene in which six of the prepared tablets were placed was hung in such a space that these tablets did not directly contact the Silica Gel Blue. Meanwhile, after filled with atmospheric pure air, the bottle was sealed, and placed stationarily in a room at constant temperature of 23° C. 90 days later, an adequate amount of water was added in the bottle, and then the bottle was shaked, whereupon components existing in the vapor phase and Silica Gel Blue were extracted. The respective amounts of the produced formaldehyde and formic acid in the extracted water were measured by MBTH and titration respectfully in the same manner as in Examples 1 through 5. The results are shown in Table 2.

COMPARATIVE EXAMPLE 2

From powdery trioxane containing neither formaldehyde nor formic acid, tablets each weighing 2.9 grams were prepared without adding ketoxime and by compressing and shaping with a tablet forming device. Then, the same procedures as in Examples 6 and 7 were conducted. 90 days later, in the sealed system in the presence of the Silica Gel Blue at 23° C., the respective amounts of the produced formaldehyde and formic acid were measured in the same manner as in Examples 6 and 7. The results are shown in Table 2.

TABLE 2

| Example No. | ketoxime (kind) | trioxane (wt %) | keto- xime (wt %) | form- aldehyde (mg) | formic acid (mg) |
| --- | --- | --- | --- | --- | --- |
| 6 | acetoxime | 99.5 | 0.5 | 6.0 | n.d. |
| 7 | cyclohexanone- oxime | 99.0 | 1.0 | 4.2 | n.d. |
| Comparative Example 2 | — | 100 | 0 | 263.2 | 29.8 |

Note: n.d. stands for "no detection".

EXAMPLES 8 THROUGH 12

100 grams of trioxane powder containing 30.7 ppm by weight of formaldehyde were put in a nitrogen-substituted 100 ml. four-neck flask, and melted on a hot oil bath with stirring until the temperature increased to 70° C. After adding a predetermined amount of ketoxime, the content of the flask was stirred in a melted state for 30 minutes at 70° C.

A part of this liquid was sampled, and cooled to become solid. Then, the volatile components in the sampled liquid were completely vaporized, and the vaporized components were absorbed in water. By analyzing this aqueous solution by MBTH the amount of formaldehyde in trioxane after the addition of ketoxime was measured. The results are shown in Table 3.

COMPARATIVE EXAMPLE 3

100 grams of trioxane powder containing 30.7 ppm by weight of formaldehyde were melted on a hot oil bath with stirring until the temperature increased to 70° C., and then continued stirring for 30 minutes at 70° C. without adding ketoxime. Subsequently, the same precedures as in Examples 8 through 12 were repeated, and finally the same analysis was made.

TABLE 3

| Example No. | ketoxime (kind) | trioxane (wt %) | ketoxime (wt %) | formaldehyde (wt ppm) |
| --- | --- | --- | --- | --- |
| 8 | cyclohexanone- oxime | 99.9 | 0.1 | 4.3 |
| 9 | benzoinoxime | 99.0 | 1.0 | 2.5 |
| 10 | actylacetone- dioxime | 99.5 | 0.5 | 1.5 |
| 11 | diphenylgly- oxime | 99.7 | 0.3 | 2.0 |
| 12 | dimedone- dioxime | 99.8 | 0.2 | 2.0 |
| Comparative Example 3 | — | 100 | 0 | 33.5 |

What is claimed is:

1. A stability-improved trioxane composition comprising 1,3,5-trioxane and a stabilizing effective amount of a ketoxime compound.

2. A stability-improved trioxane composition according to claim 1, in which said ketoxime compound is represented by the formula

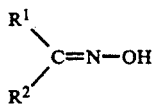   (I)

wherein each of $R^1$ and $R^2$ represent an alkyl group of up to 5 carbon atoms, a substituted alkyl group, phenyl group, a substituted phenyl group, furyl group, thienyl group, indolyl group, or lower acyl group, wherein the substituent for the alkyl group is an alkoxy group, a hydroxyl group or an amino group, and the substituent for the phenyl group is an alkyl group or an alkoxy group.

3. A stability-improved trioxane composition according to claim 1, in which said ketoxime compound is represented by the formula

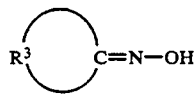   (II)

wherein $R^3$ represents an alkylene group having from 3 to 9 carbon atoms, or a diphenylene group.

4. A stability-improved trioxane composition according to claim 1, in which said ketoxime compound is represented by the formula

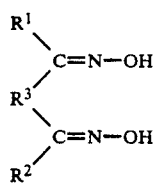   (III)

wherein each of $R^1$ and $R^2$ represents an alkyl group of up to 5 carbon atoms, an alkyl group substituted with alkoxy group, hydroxyl group, or amino group, a phenyl group, a phenyl group substituted by alkyl group or alkoxy group, furyl group, thienyl group, an indolyl group or lower acyl group, and $R^3$ represents an alkylene group having 5 to 9 carbon atoms, or a diphenylene group.

5. A stability-improved trioxane composition according to claim 1, in which said ketoxime compound is represented by the formula

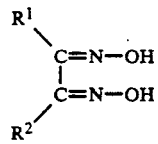   (I)

wherein each of $R^1$ and $R^2$ represents an alkyl group of up to 5 carbon atoms, a substituted alkyl group, a phenyl group, a substituted phenyl group, a furyl group, a thienyl group, an indolyl group, or lower acyl group, wherein the substituent for the alkyl group is an alkoxy group, a hydroxyl group or an amino group, and the substituent for the phenyl group is an alkyl group or an alkoxy group.

6. A stability-improved trioxane composition according to claim 1, in which said ketoxime compound is represented by the formula

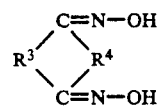   (V)

wherein each of $R^3$ and $R^4$ represents an alkylene group each having 3 to 9 carbon atoms.

7. A stability-improved trioxane composition according to claim 1, in which said ketoxime compound is represented by the formula

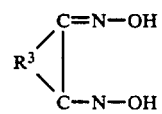   (VI):

wherein $R^3$ represents an alkylene group having 3 to 9 carbon atoms.

8. A stability-improved trioxane composition according to claim 2, in which said ketoxime compound is acetoxime, ethylmethylketoxime, diethylketoxime, methyl-n-propylketoxime, methyisopropylketoxime, methylisobutylketoxime, pinacolinoxime, di-n-propylketoxime, diisopropylketoxime, methylisoamylketoxime, acetoinoxime, methyloxyisopropylketoxime, acetophenonoxime, propiophenonoxime, butyrophenonoxime, valerophenonoxime, benzophenonoxime, benzoinoxime, 4-chloroacetophenonoxime, deacetylmonoxime, 2-acetofuronoxime or 2-acetothienonoxime.

9. A stability-improved trioxane composition according to claim 3, in which said ketoxime compound is cyclobutanonoxime, cyclopentanonoxime, cyclohexanonoxime, camphor-oxime or 9-fluolenoxime.

10. A stability-improved trioxane composition according to claim 4, in which said ketoxime compound is acetylacetone-dioxime.

11. A stability-improved trioxane composition according to claim 5, in which said ketoxime compound is dimethylglyoxime, diphenylglyoxime or furyldioxime.

12. A stability-improved trioxane composition according to claim 6, in which said ketoxime compound is dimedondioxime.

13. A stability-improved trioxane composition according to claim 7, in which said ketoxime compound is nioxime.

14. A stability-improved trioxane composition according to claim 1, in which the concentration of formaldehyde in trioxane is 100 ppm by weight or less.

15. A stability-improved trioxane composition according to claim 1, in which the content of said ketoxime compound in the composition is 0.05 to 10% by weight.

16. A stability-improved trioxane composition according to claim 1, in which the concentration of formaldehyde in trioxane is 50 ppm by weight or less.

17. A stability-improved trioxane composition according to claim 1, in which the concentration of formaldehyde in trioxane is 16 ppm by weight or less.

18. A stability-improved trioxane composition according to claim 1, in which the content of said ketoxime compound in the composition is 0.1 to 2% by weight.

* * * * *